United States Patent
Feldstein et al.

[11] Patent Number: 6,137,117
[45] Date of Patent: Oct. 24, 2000

[54] INTEGRATING MULTI-WAVEGUIDE SENSOR

[75] Inventors: Mark J. Feldstein, Washington, D.C.; Brian D. MacCraith, Dublin, Ireland; Frances S. Ligler, Potomac, Md.

[73] Assignee: The United States of America as represented by the Secretary of the Navy, Washington, D.C.

[21] Appl. No.: 09/336,729

[22] Filed: Jun. 21, 1999

[51] Int. Cl.$^7$ .................................................... G01N 15/06
[52] U.S. Cl. ........................................ 250/573; 250/461.2
[58] Field of Search .................................... 250/573, 576, 250/216, 483.1, 484.2, 458.1, 461.2; 385/12, 130, 131; 356/244, 442

[56] References Cited

U.S. PATENT DOCUMENTS 5,959,292   9/1999   Duveneck et al. .................. 250/227.11

*Primary Examiner*—Que T. Le
*Attorney, Agent, or Firm*—Barry A. Edelberg; Amy Loch Ressing

[57] ABSTRACT

A waveguide-based sensing system includes a plurality of waveguides secured within a waveguide holder. Each waveguide has a sensing surface with attached analyte recognition elements. The end faces of the sensing surfaces are perpendicular (or at least approximately perpendicular) to the sensing surfaces. The sensing surfaces are directly excited by light directed normal thereto and emit optical signals responsive to the presence of an analyte. These optical signals are coupled into the waveguides. The optical signals travel along the length of the waveguides to the end surfaces, which integrate the optical signals over the length of the waveguides. The integrated optical signals emitted from the end surfaces of the fibers are then detected and analyzed.

16 Claims, 2 Drawing Sheets

INTEGRATING MULTI-WAVEGUIDE SENSOR

BACKGROUND OF THE INVENTION

1. Field of the Invention

The present invention relates to generally to optical sensors using waveguides and more specifically to optical sensors using a plurality of waveguides.

2. Description of the Background Art

The basic technique for fluorescence excitation and detection in sensors measuring surface reactions is based on evanescent field excitation and either evanescent field or far field detection. ((See Golden et al. *An Evanescent Wave Fiber Optic Biosensor: Challenges for Real World Sensing*, reprinted from Chemical, Biochemical and Environmental Fiber Sensors IV in 1796 SPIE Proceedings Series, pp. 2–8 (Meeting 8–9 September 1992, in Boston, Mass.; published April 1993), Kroneis et al. U.S. Pat. No. 4,703,182, Oct. 27, 1987, Ligler et al. *Array Biosensor for Multi-Analyte Sensing*, SPIE Proceedings Series, in press (1998).) For single analyte detection, a principal method is a fiber-based optic biosensor (see Anderson et al., *IEEE Eng. Med. Biol.*, 13, 358–363 (1994)), which use both evanescent field excitation and detection. Although highly successful, it has been found that the sensitivity of this method is limited, in part, by the unavoidable background of excitation light. Technologies for multi-analyte, multi-sample detection such as the array biosensor which uses evanescent field excitation from a planar waveguide and point by point imaging in the far field with a CCD are also susceptible to background scatter from the excitation light (see Feldstein et al., *J. Biomed. Microdevices*, 1, 139–153 (1999)). In addition, CCD imaging for biosensor applications is limited by the cost of a high quality imaging element and the requisite signal collection and processing power.

Evanescent field excitation of bound fluorophores has the benefit of localizing the excitation field at the sensor surface. This allows, in principle, detection of bound species even in the presence of unbound fluorophores in the bulk solution. However, in practice, bulk excitation and scatter are significant, and measurements are typically made in the absence of a bulk solution. Moreover, the evanescent field generated by total internal reflection at an interface is weak (in the absence of an enhancement mechanism such as surface plasmon polariton excitation) as compared to that which can be achieved by direct illumination from a source of equivalent power.

The issue of the lateral confinement of the optical excitation and signal is also of significant import to these optical methods, especially with respect to the array system. Specifically, when using a single planar waveguide to distribute excitation to multiple recognition elements, there can be cross talk between the elements since there is an absence of lateral optical confinement between these elements. Moreover, uniformity of excitation is difficult to achieve in a laterally multi-mode waveguide. Hence, recognition elements may be exposed to differing excitation intensities, thus making a single uniform system calibration impossible.

Finally, spatially distributed recognition elements (which yield spatially distributed fluorescence) have consequences for optical detection methods and signal to noise optimization. For example, in biosensors utilizing CCD imaging, the detection sensitivity is limited by the large number of pixels, each of which have inherent noise. Based on considerations such as this, it would be preferable to spatially integrate all the fluorescent emission to a single detection element.

SUMMARY OF THE INVENTION

Accordingly, it is an object of this invention to provide a multi-waveguide sensor having an increased sensitivity.

It is a further object of the present invention to provide a multi-waveguide sensor that minimizes cross-talk between the waveguides.

It is another object of some embodiments of the present invention to provide a multi-waveguide sensor which enhances discrimination between background excitation and an emitted signal.

These and additional objects of the invention are accomplished by a waveguide sensor including a plurality of waveguides mounted on a support. The end surface of each waveguide is essentially perpendicular to its sensing surface. Excitation light directed approximately normal (but below the critical angle) to and incident upon the sensing surfaces directly illuminates and excites the luminescent species on, within, or near the sensing surface of the respective waveguide, causing it to emit light. This emitted light is coupled into the respective waveguides. A detector is positioned at the end surface of at least one of the waveguides. Each waveguide in the sensor integrates, along its length, the emitted light that has been coupled into it. The detector or sensor may be moved to allow detection at each waveguide end, or a plurality of detectors may be employed to permit simultaneous detection from various waveguides. If desired, a spatial filter normal to the sensing surface of the waveguide (i.e., approximately perpendicular to the end surface of the waveguide, and below the critical angle) spatially filters excitation light from emitted light and/or spatially discriminates between emitted light at different wavelengths.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

Figure 1:
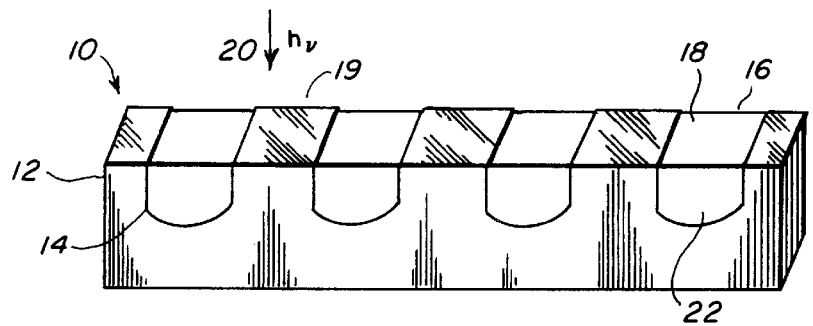
FIG. 1 shows an integrated waveguide array according to the present invention.

In the present invention, a plurality of waveguides are secured on a substrate/support. The waveguides are mounted within the support in such a manner that the analyte-sensing surfaces (the surfaces having an analyte recognition species attached) may be exposed to a fluid sample. The support may be any material capable of holding waveguides but is preferably opaque (for example black) or reflective (for example aluminum or stainless steel) to eliminate or minimize cross-talk between the waveguides secured thereon. To facilitate mounting of the waveguides to the support, the support surface on which the waveguides are mounted may include depressions, gratings, hooks, ring supports, or any other mechanism that assists in stabilizing the position and alignment of the mounted waveguides on the support. The number of attachment points between the waveguides and the support is not critical, provided that the waveguides are firmly fixed held thereon. Each waveguide is typically associated with a unique fluid channel, so that a single sensing device can simultaneously analyze multiple samples.

If desired, cross-talk between various waveguides may be minimized by the use of a non-transparent substrate. This substrate will either absorb or scatter excitation light and stray fluorescent emission rather than allowing their transmission to other waveguides. The efficient optical throughput of waveguides may be enhanced by cladding the waveguides (at least the non-sensing surfaces thereof) with a low-refractive index material. For example, this low refractive index material may be Teflon™, or may be an epoxy used to secure and/or seal the waveguide to the substrate. Also, at locations where the waveguide is not in contact with the substrate, air serves as a highly effective cladding.

Each waveguide has an analyte-sensing surface with molecular recognition elements thereon. A wide variety of molecular recognition elements and methods for coating molecular recognition elements on waveguides may be used with the present invention. For example, the analyte-sensing surface of the waveguide surface may be sensitized to an analyte by attachment with or otherwise coating with a biomolecular recognition species. In such a case, the biomolecular recognition species is typically a protein (e.g., an antibody, an antibiotic, an antigen target for an antibody analyte, a cell receptor protein), a nucleic acid (e.g., DNA and RNA), a cell, or a cell fragment.

Molecular recognition on the analyte-sensing surface may also be accomplished by means other than the attachment of a biomolecular recognition species. For example, the analyte-sensing surface may be formed by coating a surface of the waveguide with a doped or undoped polymer or sol-gel that exhibits a differential optical response upon exposure to the analyte or the analyte in combination with an additional label or labels. An example of one such non-biomolecular recognition species is provided in MacCraith, B D, *Sensors and Actuators B.*, 29:(1–3) 51–57 October 1995, the entirety of which is incorporated herein for all purposes.

Regardless of how analyte responsiveness is achieved, a label is typically used to generate an optical signal indicative of the presence of absence of the analyte. Typically, the label is a luminescent label (such as a fluorescent label or a phosphorescent label). If a sandwich assay is desired, the labeled secondary molecular species may be any labeled species that recognizes a molecular binding site on the bound analyte or the immobilized biomolecular recognition species/bound analyte complex.

If the surface of the analyte-sensing surface is coated with biomolecular recognition species, either a competitive assay (labeled and unlabeled analytes compete for open binding sites), a displacement assay (unlabeled sample analyte dissociates bound, labeled analyte/biomolecular recognition species) on a waveguide that has been previously saturated with bound, labeled analyte) or a sandwich assay (sample analyte binds to a primary biomolecular recognition species on the waveguide surface, and a labeled secondary molecular species that binds to the immobilized analyte or the immobilized analyte/primary molecular species complex), or any other type of bioaffinity/chemical assay may be employed.

The waveguide may be any material transparent to the excitation light and into which evanescent emitted light may be coupled. Glass, thermoplastics, polymers, sol gels, and optical epoxies commonly used by the art may be used as waveguides in the present invention. The waveguides may be solid (i.e., non-hollow, e.g., fiber or planar waveguide) or hollow (e.g., capillary waveguide). Typically, the waveguides are elongated so as to have a long axis and a short axis, and are positioned within the substrate parallel to each other and also so that in use, sample flow occurs along the longitudinal axes of the waveguides. This arrangement allows the device of the present invention to simultaneously assay several fluid samples.

Additionally, the waveguides typically have flat surfaces, and are most often planar. Nevertheless, waveguides having other shapes, even cylindrical, may be used in the present invention. The waveguides may be formed either directly in the supporting substrate, via injection molding, for example, or formed independently and joined later to the support substrate. Similarly, waveguides may be formed in an integrated fashion in a substrate and a flow cell for sample and reagent subsequently introduced through the channels. Finally, these fabrication methods are ideally suited for forming more complex structures, such as tapered waveguides to further optimize performance.

The sensor of the present invention exploits the phenomenon of evanescent wave capture of luminescence where the luminescent species are excited by direct illumination that is incident normal to the plane of the waveguide rather than by the evanescent field of excitation light in the waveguide. When this occurs, a significant fraction of the fluorescence emitted within the evanescent zone of the waveguide is trapped in guided modes of the waveguide, with higher order modes exhibiting greater capture efficiency. For this reason, the device typically employs multi-mode waveguides. In addition, a sensor based on multi-mode waveguides, which typically has dimensions in the range of 250–1000 microns, provides the additional advantage of being easier to fabricate and manipulate than mono-mode waveguides, which require thickness control and alignment accuracy on the sub-micron scale.

Light emitted by the labels at a frequency different from that of the excitation light is coupled, via an evanescent field, into the waveguides. The waveguides spatially integrate this coupled emission along their lengths. At the end faces of the waveguides, the emission light, along with any scattered excitation light, emerges from the waveguides. As stated above, the angular distribution of light exiting a waveguide is wavelength dependent, with shorter wavelengths exciting at greater angles. (see Gouin et al., *Fluorescence Capture by Planar Waveguides as a Platform for Optical Sensors* presented at EUROPTRODE IV in Muenster, Germany, Mar. 29–Apr. 1, 1998, p253 in the book of abstracts.) Thus, spatial filtering of the waveguide output selects the longer wavelength fluorescence signal and rejects the excitation light background. Specifically, optics, such as one or more mirrors, one or more apertures, and/or one or more optical filters, can be employed to block the higher frequency excitation light emitted at steeper angles yet pass, without any attenuation, the lower frequency fluorescence light emitted at shallower angles. This configuration represents a significant advance over the collection and detection of all light at the end of the waveguide since this latter method fails to address totally the practical problem of a signal background due to scattered excitation light being captured in the waveguide. Further, wavelength-dependent spatial filtering and detection have advantages over optical filtering alone, such as that necessary for fluorescence imaging applications, where the fluorescence signal is always attenuated by the filter and discrimination ratios of greater than $10^5$–$10^6$ are difficult to achieve. Where each waveguide is patterned with a plurality of different recognition elements, and each analyte is detected via a label that emits light at a different frequency, wavelength separation may also be conveniently used to separate emissions from different fluorophores. If patterning with multiple recognition elements is desired, patterning may be achieved by a variety of well-known methods, such as selective photolithographic activation of a coating attached to the waveguide or physical isolation methods such as ink jet printing, screen printing, or stamping.

A unique additional feature of using direct illumination and evanescent field capture in the current configuration is the lateral confinement of the captured light due to the narrow width of the waveguide elements. Incorporation of an array of narrow, uncoupled waveguides enables localized detection of the fluorescence signal from each guide without either reduction of the optical flux, due to spreading out laterally in the guide, or cross talk between the individual guides. The width of the waveguide, for the purposes of an operational sensor, can be as small or smaller than the width of available detector elements. Smaller guides will enhance the potential for greater levels of device integration but will also limit the sensor's dynamic range. That is, as the sensing area is reduced both the maximum number of analyte capture sites and the proportional maximum number of bound fluorophores decrease thereby setting an upper limit on the detection concentration after which the signal is saturated. The sensor described herein, however, is able to minimize the overall device size while maximizing sensitivity and dynamic range by utilizing the majority of the waveguide surface area for recognition molecules and then spatially integrating all surface bound fluorescent emission to a single detector.

A broad range of excitation configurations are possible. The selection among alternatives will depend, in part, on the type of recognition element patterning on the waveguide:

(i) Single recognition element per guide.

For a single antibody per guide, diffuse excitation over entire guide is usually favored since (1) it has the practical advantage of 'no moving parts', especially important for fieldable devices, (2) it is the simplest configuration with respect to signal detection/processing since entire guide is always illuminated, and (3) there would be minimal issues of alignment since the illumination is permanently fixed over the entire substrate. Diffuse excitation can be achieved with a number of low cost techniques. Possibilities include, but are not limited to, (1) the shaped (via diffractive optical element) output of a diode laser, (2) an LED array, where the LEDs are aligned to match the spatial distribution of the waveguides, or (3) a broad beam non-coherent light source (ex., incandescent lamp) with monochromatic filter.

An alternate to diffuse excitation would be line pattern excitation (i.e., non diffuse) scanned along waveguide and integrated signal detection/processing. This method has several advantages. These advantages include (1) greater excitation intensity per unit area vs. diffuse excitation (given light sources of equal power), (2) the ability to tightly control and potentially manipulate the angular distribution of the excitation light, and (3) the potential for using high sensitivity, background and noise rejecting electronic signal processing methods (ex., lock-in amplification).

(ii) Multiple recognition elements per guide

For the cases of multiple antibodies per guide, possible alternate excitation configurations include either stepped (or oscillated) linear excitation or excitation from an addressable multi-element array of sources. Stepped (or oscillated) linear excitation to sequentially probe each patterned region has the advantages of enhanced signal processing/detection capabilities via synchronized detection to stepping (oscillating) excitation and lock-in amplifier signal processing. Stepping (or oscillation) can be achieved by a number of methods, including: (1) diffractive acousto-optical element(s), (2) stepper motor positioning of the excitation beam, or (3), use of a rotating scanner element, such as a commercially available galvo scanner.

Alternatively, an addressable multi-element array of optical sources, such as LEDs, can be used to sequentially probe each patterned region. This would be a particularly low cost technique, it has the advantage of 'no moving parts', and it is inherently more flexible than stepped or oscillated excitation since LEDs (or groups of LEDs) would be addressable in any arbitrary temporal or spatial sequence.

Signal detection can be accomplished by use of a variety of different linear detector arrays, such as photodiodes, a linear CCD, a PMT array, or a CMOS linear image sensor. Alternately, if only a single waveguide is read at a given time then the device need only employ a single detector element if appropriate collection optics are employed to direct the output of each guide to a single spatial location. In many cases it may not be necessary to use collection optics—e.g. it may be sufficient for the device to employ a detector array with integrated filter butt-coupled to the waveguide. If lensing is required, a linear lens array in registration with the channels may be used. Additional options include the use of a pair of linear GRIN lens arrays configured to provide a quasi-collimated region between the arrays for insertion of an interference filter, or an array of cylindrical lenses.

FIG. 1 shows a typical embodiment of a multi-waveguide sensor 10 according to the present invention. Substrate 12 includes depressions 14. Waveguides 16 are mounted within and supported by depressions 14. Analyte-sensing surfaces 18 includes attached molecular recognition elements. Labeled analogs of the analyte, or complexes of label and analyte, when attached to the surfaces 18, directly or indirectly, via the molecular recognition elements, are excited by excitation light 20, causing the label to emit light. The resulting emission is coupled into waveguides 18 via an evanescent wave. In the FIG. 1 embodiment, excitation light 20 is transmitted through the sample to the molecular recognition elements on analyte-sensing surfaces 18. Generally, the surface 19 of substrate 10 between depressions 14 is raised in comparison with the analyte-sensing surfaces of waveguides 16, to facilitate the formation of distinct sample flow channels registering, at least approximately, with individual waveguides 16 when surface 19 of device 10 is pressed against another surface (not shown). Of course, a similar separation between the sample flow channels corresponding to each upper surface 18 of each waveguide 18 may be obtained by having corresponding raised portions on the other surface in addition to or instead of on surface 19. As will be seen latter, the waveguide array of the present invention may also be configured so that the excitation light originates on the backside of the waveguide and passes through the waveguides to the analyte-sensing surfaces. This latter configuration minimizes scattering and interference from the sample fluid.

Figure 2:
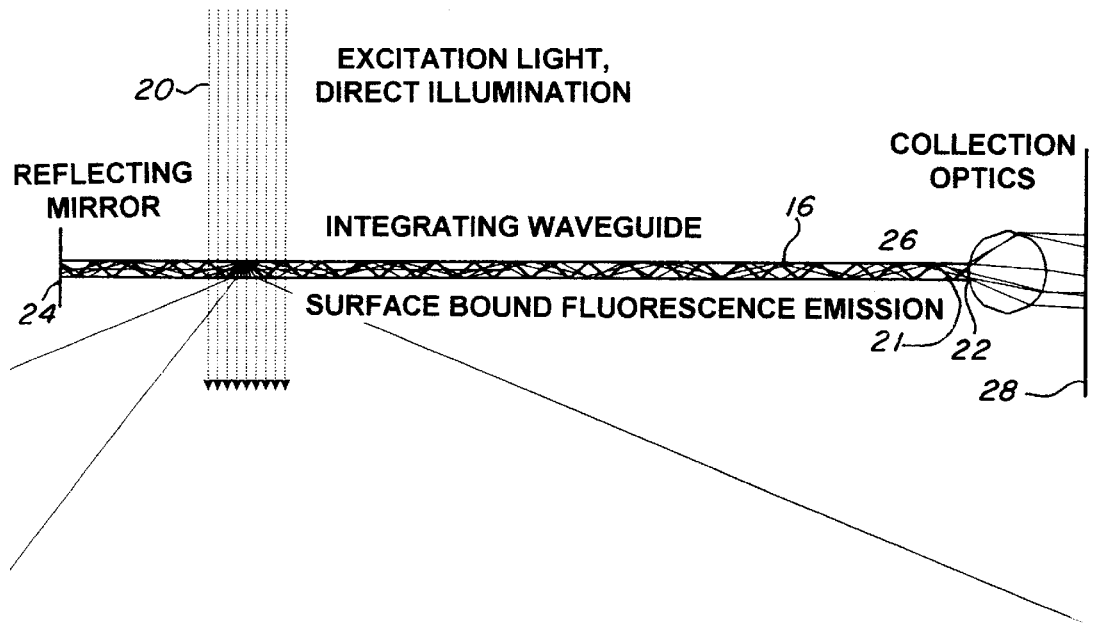
FIG. 2 shows a schematic side view of an integrating waveguide in a device according to the present invention.

As shown in FIG. 2, waveguide 16 conveys this emitted light energy 21 to light collecting end 22. Reflecting mirror 24, at the opposite end of waveguide 16 from collecting end 22, prevents loss of emitted light energy 22 by reflecting it along waveguide 16 toward collecting end 22. Collection optics 26, e.g., a lens or set of lenses and/or mirrors, directs the light energy exiting collecting end 22 upon detector 28. Collection optics 26 may be a single detection device or any array thereof for simultaneously detecting emission from several waveguides or several emission wavelengths that have been spatially separated. Both detector 28 and device 10 may be stationary, or they may be moved relative to each other to allow a single detector to detect spatially separate signals from a plurality of waveguide ends and/or a plurality of spatially separated emission frequencies.

Figure 3:
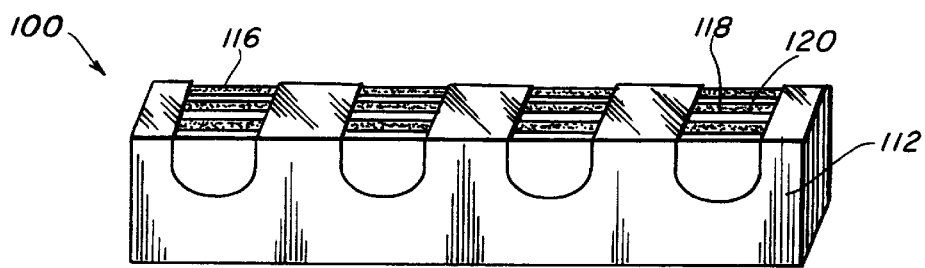
FIG. 3 shows an embodiment of the integrated waveguide array of the present invention in which each single waveguide recognizes multiple analytes.

FIG. 3 shows a waveguide sensing system 100 in which each waveguide 116 on substrate 112 has an analyte-sensing surface 118 patterned with spatially distinct regions for multiple analytes, with each analyte recognition region 120 including molecular recognition elements for a unique analyte. Each waveguide 116 may have the same or different patterned analyte-sensing surface as any other waveguide in device 100. As with FIG. 1, raised regions between the waveguides 116, either on substrate 100 or on a surface mated therewith, provide separate, individual fluid flow channels longitudinally along the extent of each waveguide 116. Thus, the FIG. 3 embodiment not only allows for simultaneous assaying of multiple samples, but for simultaneous sampling of multiple samples, each for a plurality of analytes.

In the case of a single-antibody coating, when an assay is performed, each such waveguide confines the captured fluorescence within the channel dimensions and guides it to one of the end-faces, where it can be detected. In the case of multiple antibodies patterned over the length of each waveguide, different regions of the waveguide can be sequentially illuminated and/or different fluorophores may be used for each element if it is important to distinguish which analyte was bound. Because different wavelengths of light will exit the end of waveguides 116 at different angles, exiting fluorophore emissions at different wavelengths may be spatially separated by well-known optical methods and directed to different detectors or to different regions of a detector such as a CCD detector.

In FIG. 1, FIG. 2, and FIG. 3, the waveguides are cladded by the sample on the analyte-sensing surface and the remaining surfaces are cladded by the substrate. The FIG. 4 device enhances confinement of the excitation and emission light by cladding waveguides 216 on analyte-sensing surface 218 with the sample, on surfaces 217 and 219 with substrate 202, and on surface 221 with air. The inclusion of an air cladding on at least one surface of waveguides 216 enhances light confinement. Additionally, analyte-sensing surfaces 218 of the FIG. 4 embodiment may be excited with light transmitted either through the fluid sample or light impinging normal, or essentially normal, to sides 221 and transmitted through waveguides 216. Otherwise, the FIG. 4 embodiment operates analogously to those shown in FIG. 1, FIG. 2, and FIG. 3.

Figure 5:
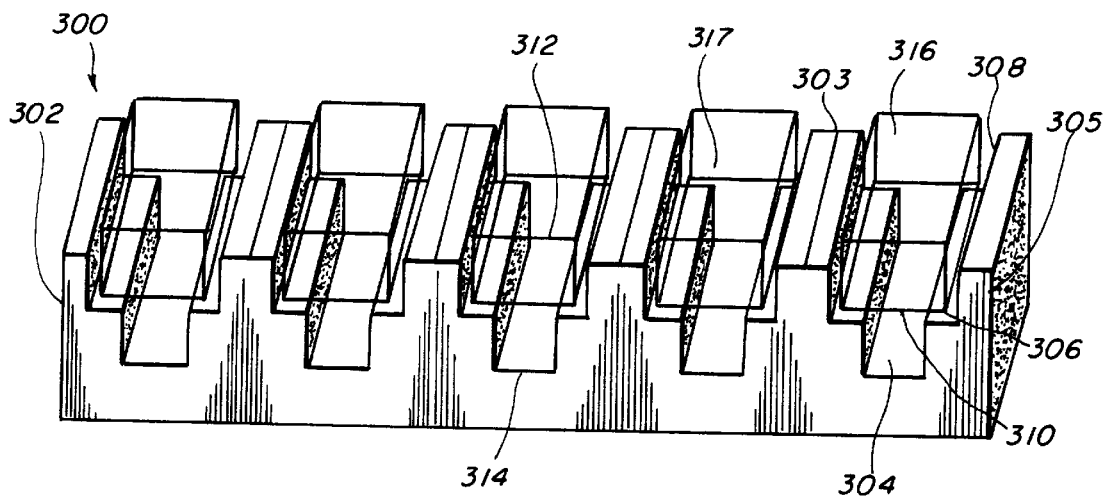
FIG. 5 shows an embodiment of the integrated waveguide array of the present invention in which the substrate upon which the waveguides are mounted includes flow channels.

FIG. 5 shows an optical assay device 300 according to the present invention in which substrate 302 includes flow channels 304 therein. Waveguides 316 rest upon shoulders 306 of depressions 308 in substrate 302. The surfaces of waveguides 316 that rest upon shoulders 306 are the analyte-sensing surfaces 310 of waveguides 316. If desired, waveguides 316 may be secured to sides 303 and 305 (and optionally shoulders 306) of substrate 302 by a transparent adhesive layer that also serves as a cladding. Fluid flow channels 304 are formed by the spaces between analyte-sensing surfaces 310 and the bottoms of depressions 308. If an adhesive is used, analyte-sensing surfaces 316 and their opposing surfaces 317 are typically free of adhesive cladding. During operation, fluid channels 308 receive a fluid sample from a supply thereof, typically via tubes (not shown) connected (for example, by press fitting or a coupler) to inlets 312 for flow channels 308. Similarly, the fluid sample exits flow channels 308 via tubes (not shown) connected (for example, by press fitting or a coupler) to outlets 314 for flow channels 308. Although FIG. 5 shows the inlets 312 and outlets 314 on the ends of waveguides 316, outlets 314 and inlets 312 for flow channels 304 may instead be provided on the bottom surface of substrate 302.

Having described the invention, the following examples are given to illustrate specific applications of the invention including the best mode now known to perform the invention. These specific examples are not intended to limit the scope of the invention described in this application.

EXAMPLES

Example 1

As illustrated in FIG. 3, an array of 5 recessed channels 1.5 mm wide by 1.5 mm deep and 20 mm long were created in a 6.35 mm thick poly(methylmethacrylate) (PMMA). These channels were filled with a high refractive index optical epoxy. When cured, the high index epoxy functioned as a waveguide, the lower index PMMA substrate provided cladding on three sides, and the sample served as the cladding on the fourth side.

Example 2

Figure 4:
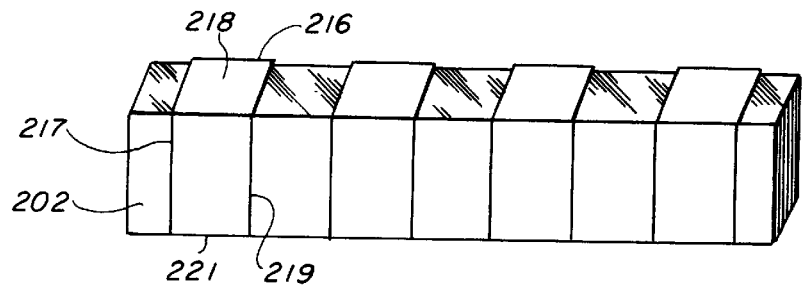
FIG. 4 shows an embodiment of the integrated waveguide array of the present invention in which the surface opposite the sensing surface is air-clad.

As illustrated in FIG. 4, an array of 6 channels that were each 1.5 mm wide were created in 3 mm thick PMMA. These channels penetrated through the entire thickness of the substrate. After temporarily sealing one side, the channels were filled with a high refractive index optical epoxy. When cured, the high index epoxy functioned as a waveguide, the lower index PMMA substrate as its cladding on two sides, air serves as the cladding on the third side, and the sample itself served as the cladding on the fourth side.

Example 3

As illustrated in FIG. 5, an array of five channels were prepared in a PMMA substrate. Individual glass waveguides were inserted into the channels to create waveguide-capped flow channels. The waveguides were sealed into the channels using a low refractive index epoxy, which also served as optical cladding to confine the captured fluorescence.

Testing of the evanescent wave capture phenomenon, relative capture efficiency, and excitation-fluorescence discrimination for the above devices were carried out using several different excitation sources and configurations. First, a collimated diode laser was used. Second, a divergent diode laser was used. Third, a filtered incandescent lamp was used. The waveguide output was measured with the waveguide 'clean' and with fluorescent dye solutions of varying concentration. In all cases, some excitation light is captured by the waveguide. However, with the inclusion of optical filters, the majority signal was due to fluorescence.

Figure 6:
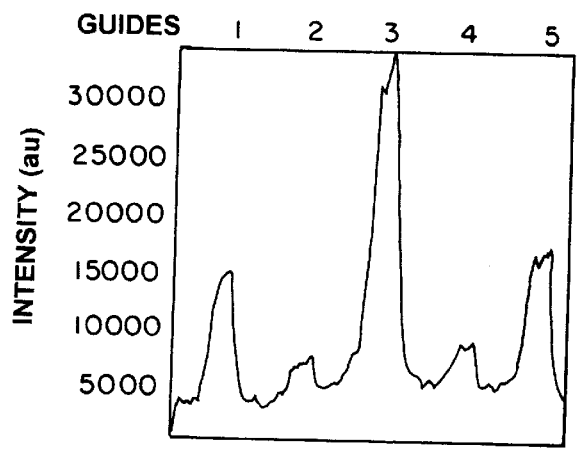
FIG. 6 is a graph showing the intensity profile of a CCD image made of the integrated waveguide array of FIG. 3 after exposing the waveguide array to a dye.

Results for the device depicted in FIG. 5 are given in FIG. 6. A CCD image of the proximal ends of the five element device of Example 3 with integrating glass waveguides, was recorded using direct illumination from a optically filtered incandescent lamp. FIG. 6 is a cross section profile of the detected optical intensity. Three of the five waveguides in this device, specifically numbers 1, 3, and 5, were coated with a fluorescently labeled antibody while the other two, number 2 and 4, were uncoated. As shown in the FIG. 6, the guides coated with fluorescent dye yielded a significant signal as compared to the background represented by uncoated guides 2 and 4. The data demonstrated three capabilities of the invention. First, the waveguides were optically independent due to the lateral confinement resulting from their narrow width as well as due to the blocking ot inter-waveguide cross-talk by use of a non-transparent substrate. Second, direct illumination was an efficient means of exciting surface bound fluorescence. Third, the fluorescent light was integrated within each of the waveguides and delivered to the detector.

Obviously, many modifications and variations of the present invention are possible in light of the above teachings. It is therefore to be understood that, within the scope of the appended claims, the invention may be practiced otherwise than as specifically described.

What is claimed is:

1. A waveguide sensing system comprising:
   a plurality of waveguides, each waveguide having a first surface, a second surface opposing said first surface, and an end surface essentially perpendicular to said first and second surfaces, said first surface of each of said waveguides having analyte recognition elements thereon;
   a waveguide holder to which each of said waveguides are secured;
   an optical detector positioned opposite said end surface of at least one of said waveguides.

2. The waveguide sensing system of claim 1, wherein each of said waveguides is elongated along an axis, and each of said end surfaces is perpendicular to each said respective axis of elongation.

3. The waveguide sensing system of claim 2, wherein each of said waveguides is a planar waveguide.

4. The waveguide sensing system of claim 2, wherein each of said waveguides is a cylindrical waveguide.

5. The waveguide sensing system of claim 2, wherein each of said waveguides is a hollow waveguide.

6. The waveguide sensing system of claim 2, wherein each of said waveguides is a non-hollow waveguide.

7. The waveguide sensing system of claim 1, further comprising a plurality of luminescent species attached, directly or indirectly, to some of said analyte recognition elements at spatially distinct locations along each of said first surfaces, wherein each of said waveguides captures and integrates to said each said respective end face and said detector, light emitted by said luminescent species.

8. The waveguide sensing system of claim 1, further comprising a source of excitation light directed essentially perpendicularly toward said analyte recognition elements on said first surface of at least one of said waveguides.

9. The waveguide sensing system of claim 1, wherein said analyte recognition elements on said first surface of each respective waveguide are patterned to forms spatially distinct regions for recognizing multiple distinct analytes.

10. The waveguide sensing system of claim 9, further comprising a plurality of light sources, each of said light sources being aligned to direct light exclusively to one of said spatially distinct regions on one or more of said waveguides.

11. The waveguide sensing system of claim 1, wherein said holder optically insulates each said waveguide from scattered emission and uncaptured luminescence emission from other waveguides secured to said holder.

12. The waveguide sensing system of claim 1, wherein said holder includes channels, each of said channels directing a sample fluid to said recognition elements on a respective one of said first surfaces of a respective one of said waveguides.

13. A method of detecting an analyte, comprising the steps of:
   exposing, to a sample fluid suspected of containing said analyte, a first surface of at least one waveguide of a plurality of waveguides secured to a waveguide holder, each of said waveguides including a first surface, a second surface opposing said first surface, and an end surface essentially perpendicular to said first and second surfaces, said first surface of each of said waveguides having analyte recognition elements thereon;
   directing a source of excitation light essentially perpendicularly toward said first surface of said at least one waveguide, the presence of said analyte attached to said analyte recognition elements on said at least one waveguide being detectable by the light emitted at said sensing surface and coupled into said at least one waveguide;
   detecting said emitted light with an optical detector positioned opposite said end surface of at least one waveguide.

14. The method of claim 13, wherein each of said waveguides is elongated along an axis, and each of said end surfaces is perpendicular to each said respective axis of elongation.

15. The method of claim 14, wherein said analyte recognition elements on said first surface of each respective waveguide are patterned to forms spatially distinct regions for recognizing multiple distinct analytes.

16. The method of claim 13, wherein said holder includes channels, each of said channels directing a sample fluid to said recognition elements on a respective one of said first surfaces of a respective one of said waveguides.

* * * * *